(12) United States Patent
McLeod et al.

(10) Patent No.: US 6,607,497 B2
(45) Date of Patent: Aug. 19, 2003

(54) NON-INVASIVE METHOD FOR TREATING POSTURAL INSTABILITY

(75) Inventors: Kenneth J. McLeod, Stony Brook, NY (US); Clinton T. Rubin, Port Jefferson, NY (US)

(73) Assignee: The Research Foundation of the State University of New York (SUNY), Stony Brook, NY (US)

(*) Notice: Subject to any disclaimer, the term of this patent is extended or adjusted under 35 U.S.C. 154(b) by 39 days.

(21) Appl. No.: 09/739,426

(22) Filed: Dec. 18, 2000

(65) Prior Publication Data

US 2002/0077570 A1 Jun. 20, 2002

(51) Int. Cl.[7] ............................................. A61B 5/103
(52) U.S. Cl. ........................................................ 600/595
(58) Field of Search .............................. 600/587, 594, 600/595, 552, 553

(56) References Cited

U.S. PATENT DOCUMENTS 5,103,806 A   4/1992  McLeod et al.
6,234,975 B1 * 5/2001 McLeod et al. ............ 600/552

FOREIGN PATENT DOCUMENTS

WO    WO 99/07280    2/1999

OTHER PUBLICATIONS

Vibration–Induced Postural Posteffects, by M. M. Wierzbicka, J. C. Gilhodes, and J. P. Roll, 1998, The American Physiological Society, pp. 143–149.

Relevance to Musculoskeletal Conditions, by McLeod, Dusatko, Labruzzo, and Rubin, 44th Annual Meeting, Orthopaedic Research Society, Mar. 16–19, 1998, New Orleans, Louisiana, 1 pg.

Postural Stabilization on a Moving Platform Oscillating at High Frequencies, by I. Pyykko, H. Aalto, J. Starck, and H. Ishizaki, Reprint & Copyright by Aerospace Medical Association, 1993, pp. 300–305.

* cited by examiner

*Primary Examiner*—Max F. Hindenburg
*Assistant Examiner*—Pamela Wingood
(74) *Attorney, Agent, or Firm*—Dilworth & Barrese LLP

(57) ABSTRACT

A method is provided for treating postural instability following a determination that a patient is experiencing postural instability. The method includes the steps of (a) providing a vibration table having a non-rigidly supported platform; (b) permitting the patient to rest on the non-rigidly supported platform for a predetermined period of time; and (c) repeating the steps (a) and (b) over a predetermined treatment duration. Step (b) includes the steps of (b1) measuring a vibrational response of the patient's musculoskeletal system using a vibration measurement device; (b2) performing a frequency decomposition of the vibrational response to quantify the vibrational response into specific vibrational spectra; and (b3) analyzing the vibrational spectra to evaluate at least postural stability. Preferably, the predetermined period of time is approximately 10 minutes and the predetermined treatment duration is at least four weeks.

20 Claims, 2 Drawing Sheets

NON-INVASIVE METHOD FOR TREATING POSTURAL INSTABILITY

BACKGROUND OF THE INVENTION

1. Technical Field

This disclosure relates to a medical treatment procedure. More particularly, the disclosure relates to a non-invasive method for treating postural instability.

2. Description of the Related Art

Falls represent a serious medical problem in the United States. As one example, consider that some 250,000 individuals fall each year fracturing their hip. This generally results in total hip arthroplasty or hip replacement surgery at a significant cost. Health care costs in this area range in the billions of dollars per year in the United States alone. Further, the morbidity associated with hip fractures is extensive. Half of all individual who undergo total hip arthroplasty will not achieve their previous level of motility and will require assistance to walk. Moreover, for patients over 70, more than one-half will die within 12 months of a hip fracture due to complications associated with the surgery or extended bed rest following surgery. Other consequences as a result of falling include lost wages, lost productivity, upper extremity injuries, head injuries, fear of falling leading to decreased physical activity, etc.

The primary cause of falling is loss of balance, and the inability to re-achieve balance once it is lost, concepts referred to as postural instability or imbalance. Postural instability is closely tied to the status of the neuro-muscular system, though a thorough understanding of the factors that lead to, or detract from, postural stability has yet to be established.

To prevent individuals from falling and injuring themselves due to postural instability, a method is needed for treating postural instability or imbalance.

SUMMARY OF THE INVENTION

The present disclosure describes a method for treating postural instability following a determination that a patient is experiencing postural instability. Postural instability, due, for example, by the onset of senile sarcopenia, is determined by measuring non-invasively, the vibrational characteristics of the musculoskeletal system and analyzing the same, as described in U.S. Pat. No. 6,234,975 B1, granted to McLeod et al., entitled Non-Invasive Method of Physiologic Vibration Quantification, the contents of which are incorporated herein by reference.

In particular, the present disclosure relates to a non-invasive method for treating a patient experiencing postural instability including the steps of (a) providing a vibration table having a non-rigidly supported platform; (b) permitting the patient to rest on the non-rigidly supported platform for a predetermined period of time; and (c) repeating the steps (a) and (b) over a predetermined treatment duration. Step (b) includes the steps of (b1) measuring a vibrational response of the patient's musculoskeletal system using a vibration measurement device; (b2) performing a frequency decomposition of the vibrational response to quantify the vibrational response into specific vibrational spectra; and (b3) analyzing the vibrational spectra to evaluate at least postural stability. Preferably, the predetermined period of time is approximately 10 minutes and the predetermined treatment duration is at least four weeks.

BRIEF DESCRIPTION OF THE DRAWINGS

The invention will be described in detail in the following description of preferred embodiments with reference to the following figures wherein.

DETAILED DESCRIPTION OF PREFERRED EMBODIMENTS

Figure 1:
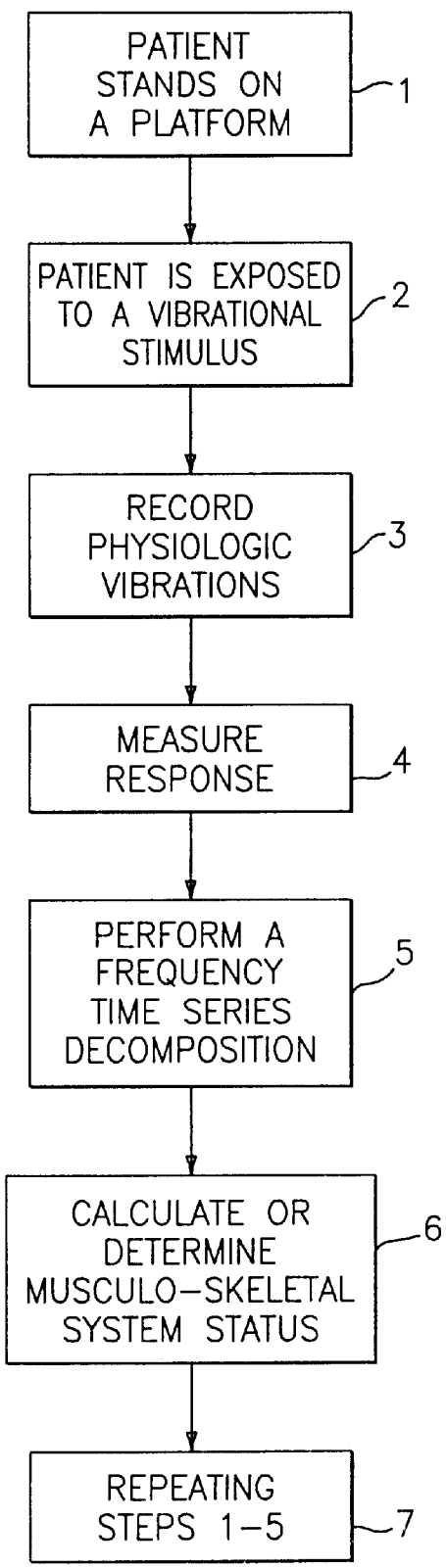
FIG. 1 is a flow diagram showing the steps for treating postural instability in accordance with the method of the present disclosure.

The present disclosure describes a method for treating postural instability after determining a patient is experiencing postural instability. A method and system for determining if a patient is experiencing postural instability is described in U.S. Pat. No. 6,234,975 B1, granted to McLeod et al., entitled Non-Invasive Method of Physiologic Vibration Quantification, the contents of which are incorporated herein by reference.

Once the patient is determined to be experiencing postural instability, the patient can be treated by the method of the present disclosure. In a preferred embodiment, an individual stands on a non-rigidly supported standing platform with an accelerometer attached on the outboard side of the platform so that the accelerometer is capable of sensing medial-lateral sway.

The standing platform rests on motorized spring mechanisms which cause the platform to move when they are turned on. Alternatively, the standing platform may rest on a plurality of springs or coils which cause the standing platform to move once a patient stands thereon. Further, the standing platform can include various compliant modalities other than springs (e.g., rubber, elastomerics, foams, etc). The movement of the standing platform enables the accelerometer to sense the medial-lateral sway of the patient's body.

In one embodiment, a cantilever beam accelerometer is used which typically employs a cantilever with one end supported on a mount and a proof mass on the other. Such a beam is typically micro-machined from silicon, and one or more strain gauges disposed on its surface at a desired sensing site. These one or more strain gauges are connected in an electric circuit to provide a signal indicative of acceleration-induced strain in the beam. The proof mass used is low in order to allow measurements at higher frequencies, since the natural frequency of the beam varies as the inverse square root of the mass. Cantilever beam strain gauge accelerometers are desirable because of their high sensitivity and their frequency response which extends down to D.C. See, e.g. U.S. Pat. No. 5,412,987 to Bergstrom et al. which is incorporated herein by reference. Alternatively, low cost solid state, variable capacitance accelerometers may be used, which, while less sensitive, are more robust.

The accelerometer records the individual's natural sway pattern while the individual preferably stands in the Romberg position (feet separated at shoulder width, hands at side, and eyes open) for a preferable period of 10–100 seconds.

The standing platform imposes vertical vibration on the patient standing thereon. The mass of the patient combined with the spring constants of the spring supports of the platform results in a spring-mass resonance system permitting the patient to be oscillated. Vibrational treatment is preferably performed at 30 Hz, for approximately ten minutes per day, at approximately 0.2 g peak-to-peak for approximately four weeks.

A study conducted using the method of the present disclosure illustrated the effect of ten minutes of daily vibrational loading on the magnitude of postural sway in a population of 15 women aged 20–60. Over the 18 days of the study (weekends were excluded, so the 18 days represent approximately four weeks of treatment), postural sway was observed to decrease by approximately 25%, with a "p" value of 0.006, indicating a significant effect of treatment.

Nine women continued in the study after four weeks. These women returned each day to have postural sway measured while standing on a non-vibrational platform for ten minutes. Postural sway was observed to increase over time and finally, returning to pretreatment levels within 14 days.

It is noted that the literature on vibrational effects on balance and postural stability clearly indicates that one should expect vibration to transiently degrade the performance of the postural control mechanisms in the body. However, the method of the present disclosure provides long-lasting, improved postural control which indicates that the means of applying vibrational loading to the skeleton is fundamentally different than established modality. This difference is attributed to the fact that the method of the present disclosure exposes the musculoskeletal system to vibration under dynamic, rather than static, postural control conditions. That is, by utilizing the sprung platform, a low-level, but distinct postural perturbation is introduced, which the postural control system must correct. Thus, the presence of a vibrational stimulus occurring concomitantly with the low frequency postural perturbance, results in significantly enhanced postural control ability.

Referring now in specific detail to the drawings in which like reference numerals identify similar or identical elements throughout the several views, and initially to FIG. 1, a flow diagram of the postural instability treatment method of the present disclosure is shown. In step 1, the patient stands on the unstable standing platform which includes at least one accelerometer mounted to the outboard side thereof. In step 2, the patient is exposed to a vibrational stimulus by the unstable standing platform. That is, the unstable standing platform causes a vibrational perturbation of the patient's neuro-sensory control system. In step 3, the vibrational perturbation causes signals to be generated within at least one of the patient's muscles to create a measurable response from the musculoskeletal system. External vibrations and/or perturbation may be employed to create a measurable musculoskeletal response. This is particularly true for voluntary muscles which may have to be flexed to stimulate them. Involuntary muscles, such as postural muscles, typically do not require external stimulation and measurable signals can be produced without external vibration or perturbation. Preferably, the patient stands on the unstable standing platform for a period of 10 minutes and the platform is vibrated at approximately 30 Hz and at 0.2 g peak-to-peak.

Step 4 represents measuring/recording the muscle response by, for example, recording musculoskeletal vibrations as indicated by the accelerometer. Thereafter, in step 5, a frequency decomposition or other time series analysis/comparison is made to determine musculo-skeletal status. Also, vibrational spectral response data is compared to previously collected vibrational spectral response data which may include data obtained for individuals with similar characteristics to the patient, for example age, sex, body measurements, etc.

Step 6 determines the musculo-skeletal status of the patient, especially if the postural stability of the patient is improving by analyzing the vibrational spectral response data obtained in step 5. Step 6 may also include analyzing the vibrational spectral response data to evaluate other neuro-muscular characteristics. Step 7 entails repeating steps 1–6, where the patient undergoes the procedure over a predetermined treatment duration. Preferably, the treatment duration is at least four weeks, i.e., the patient undergoes the procedure for 10 minutes a day over a four week period.

Figure 2:
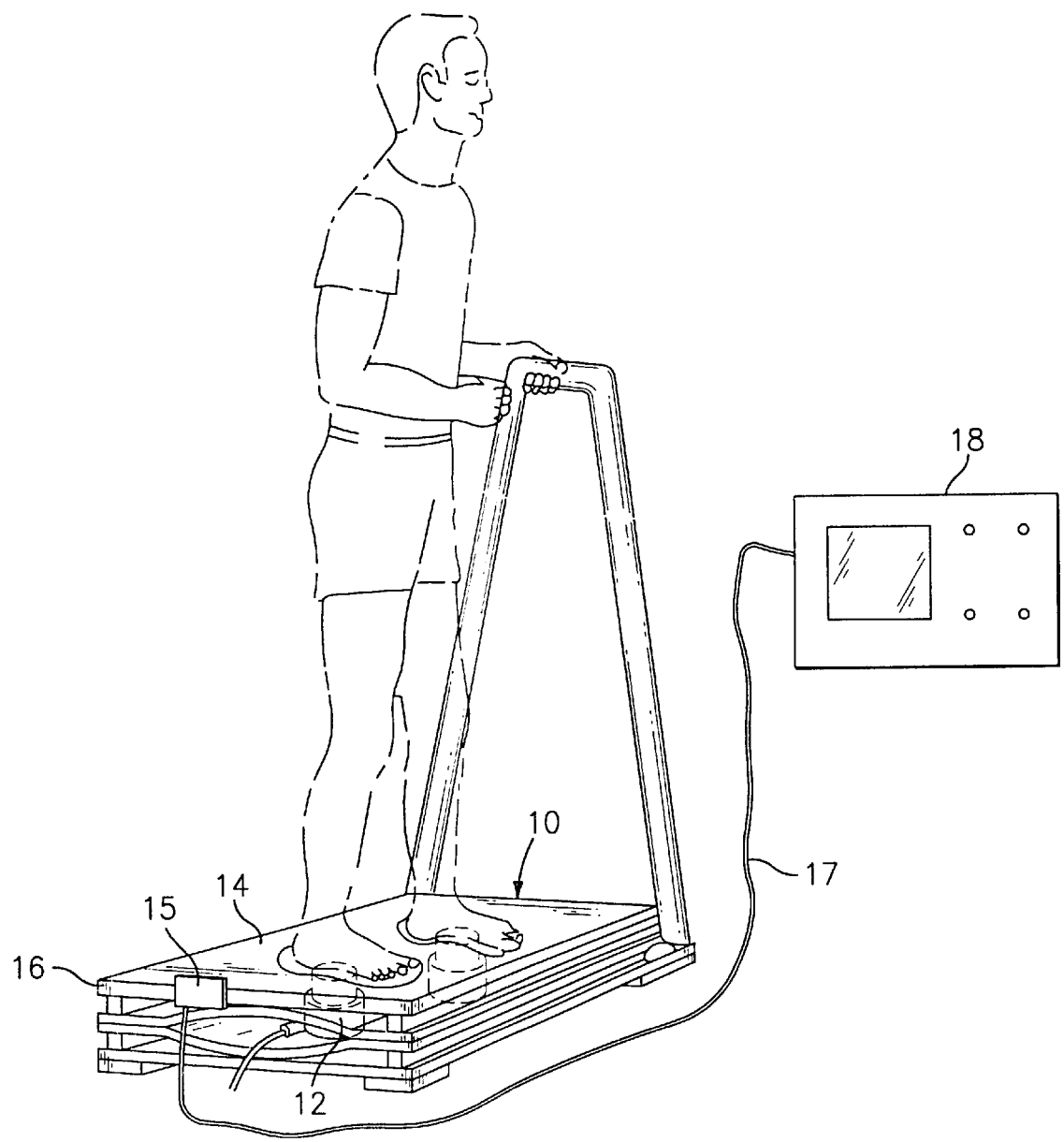
FIG. 2 is an isometric view showing a vibrating platform with a patient undergoing vibrational treatment of postural instability in accordance with the method of the present disclosure.

FIG. 2 shows a patient undergoing the treatment method according to the present disclosure. The patient stands on a vibration table 10. Vibrations, generated by table 10 for a predetermined period of time, for example, 10 minutes, are transmitted through the patient's body. The vibrations are generated by motorized spring mechanisms 12 located underneath a standing platform 14 of the vibration table 10 and attached thereto. It is contemplated that the vibrations may be generated by a plurality of non-motorized springs or coils attached underneath the standing platform 14, upon which the standing platform 14 rests.

The frequencies imparted by vibration table 10 are in the range between 30–90 Hz with a peak amplitude between 0.04 and 0.4 g. Preferably, the frequency of the vibration table 10 is approximately 30 Hz and the peak amplitude is 0.2 g. The vibration waves are preferably sinusoidal, however other waveforms are contemplated. At least one low-mass accelerometer 15 is mounted to vibration table 10 on an outboard side 16 of the standing platform 14. It is contemplated that accelerometer 15 may be mounted to the patient, for example, the patient's thigh.

Accelerometer 15 is used to measure the vibrational response of the patient's musculoskeletal system. During the vibration generation of vibration table 10, the response of accelerometer 15 can be amplified by a preamplifier (not shown) as known in the art. It is contemplated that the accelerometer 15 can be worn by the patient.

Thereafter, the vibrational response is measured and recorded by spectrum analyzer/computer 18 which is electrically connected to accelerometer 15 by a cable 17. The accelerometer response data is analyzed to extract information on postural sway. If the accelerometer 15 is attached to the patient, then one can also analyze and extract information on muscle strength and the muscle to bone stimulus to determine any improvement in the patient's neuro-muscular status.

It is contemplated that the method of the present disclosure be carried out while the patient is sitting on the unstable standing platform. Hence, the method can thus be used in the treatment of the infirm elderly where other treatments are beyond the physical capabilities of these individuals.

Advantages provided by the method of the present disclosure is that little or no training/learning is required of the patients; the apparatus utilized by the method is inexpensive to construct and its small size makes it convenient for storage and use; the frequency of vibrational loading of the standing platform can be easily adjusted to permit focused treatment on specific mechano-receptors in the postural control process, i.e., cutaneous receptors, golgi tendon organs, muscle spindles, etc.; the amplitude of vibrational loading of the standing platform can be easily controlled from 0.05 to 0.5 g; only a short duration of treatment is required for significant effect (ten minutes per day); the method provides a sustained effect on postural stability, such that improved postural stability can be maintained with only weekly or twice weekly treatments; the ability to monitor postural stability in real-time during treatment; the method can be effected while the patient is in the standing or seated position; and the method can be employed in the treatment of the infirm elderly where other treatments are beyond the physical capabilities of these individuals.

While the method of the present disclosure utilizes an unstable platform as the fundamental perturbing agent to force dynamic postural control during the application of vibrational loading, it is contemplated that any similar situation in which dynamic postural control is invoked would provide a suitable condition for employing low-level vibration to improve postural control. For example, the method can be designed to treat postural instability while the patient is seated on a non-rigid surface; while the patient is exercising on a device, such as a bicycle, treadmill, stepper, etc.; while the patient is undertaking work-like tasks, e.g., lifting objects, leaning over, etc.; and while the patient is participating in sporting activities, e.g., balance beam, tai chi, etc.

Accordingly, the method of the present disclosure improves postural stability by whole body vibration in the frequency regime of 30–90 Hz using accelerations below 0.5 g. Studies have demonstrated a 25% decrease in postural sway over a period of four weeks, with the improvement being sustained for more than two weeks following termination of treatment.

Having described preferred embodiments of a novel method of treating postural instability (which are intended to be illustrative and not limiting), it is noted that modifications and variations can be made by persons skilled in the art in light of the above teachings. It is therefore to be understood that changes may be made in the particular embodiments of the invention disclosed which are within the scope and spirit of the invention as outlined by the appended claims. Having thus described the invention with the details and particularity required by the patent laws, what is claimed and desired protected by Letters Patent is set forth in the appended claims.

What is claimed is:

1. A non-invasive method for treating a patient experiencing postural instability comprising the steps of:
   (a) providing a vibration table having a non-rigidly supported platform;
   (b) permitting the patient to rest on the non-rigidly supported platform for a predetermined period of time; and
   (c) repeating the steps (a) and (b) over a predetermined treatment duration.

2. The method as recited in claim 1, wherein step (b) comprises the steps of:
   (b1) measuring a vibrational response of the patient's musculoskeletal system using a vibration measurement device;
   (b2) performing a frequency decomposition of the vibrational response to quantify the vibrational response into specific vibrational spectra; and
   (b3) analyzing the vibrational spectra to evaluate at least postural stability.

3. The method as recited in claim 2, wherein the vibration measurement device includes an accelerometer.

4. The method as recited in claim 2, wherein step (b3) includes the step of comparing the vibrational spectra to vibrational spectra of a same category.

5. The method as recited in claim 4, wherein the category includes at least one of age, sex and body measurement.

6. The method as recited in claim 2, further comprising the step of including a preamplifier for amplifying signals transmitted by the vibration measurement device to an analyzer.

7. The method as recited in claim 1, further comprising the step of vibrating the vibrational surface in a frequency range of 30–90 Hz.

8. The method as recited in claim 1, further comprising the step of vibrating the vibrational surface at a frequency of approximately 30 Hz.

9. The method as recited in claim 1, further comprising the step of vibrating the vibrational surface in a peak amplitude range of less than 0.5 g.

10. The method as recited in claim 1, further comprising the step of vibrating the vibrational surface in a peak amplitude range of 0.04–0.4 g.

11. The method as recited in claim 1, further comprising the step of vibrating the vibrational surface at a peak amplitude of approximately 0.2 g.

12. The method as recited in claim 1, wherein the predetermined period of time is approximately 10 minutes.

13. The method as recited in claim 1, wherein the predetermined treatment duration is at least four weeks.

14. The method as recited in claim 1, further comprising the step of (b1) adjusting the frequency of vibrational loading of the non-rigidly supported platform to treat at least a particular mechano-receptor of the patient.

15. A non-invasive method for treating a patient experiencing postural instability comprising the steps of:
   (a) transferring vibrations to a musculoskeletal system of the patient for a predetermined period of time; and
   (b) repeating step (a) over a predetermined treatment duration.

16. The method as recited in claim 15, wherein the step of transferring vibrations is performed while the patient is exercising.

17. The method as recited in claim 15, wherein the step of transferring vibrations is performed while the patient is either at rest or performing a task.

18. The method as recited in claim 15, wherein the step of transferring vibrations is performed while the patient is participating in a sporting activity.

19. The method as recited in claim 15, wherein the predetermined period of time is approximately 10 minutes.

20. The method as recited in claim 15, wherein the predetermined treatment duration is at least four weeks.

* * * * *